United States Patent
Bradley et al.

(10) Patent No.: US 6,643,549 B1
(45) Date of Patent: Nov. 4, 2003

(54) CARDIAC STIMULATION DEVICE AND METHOD FOR STORING DIAGNOSTIC DATA IN AN AUTOMATIC CAPTURE SYSTEM

(76) Inventors: Kerry Bradley, 3081 Menlo Dr., Glendale, CA (US) 91208; Laurence S. Sloman, 1155 N. La Cienega Blvd., West Hollywood, CA (US) 90069

( * ) Notice: Subject to any disclaimer, the term of this patent is extended or adjusted under 35 U.S.C. 154(b) by 49 days.

(21) Appl. No.: 10/003,953

(22) Filed: Oct. 30, 2001

(51) Int. Cl.$^7$ .............................................. A61N 1/362
(52) U.S. Cl. ................................................. 607/28
(58) Field of Search ........................................ 607/4–28

(56) References Cited

U.S. PATENT DOCUMENTS

| | | | |
|---|---|---|---|
| 4,513,743 A | 4/1985 | Van Arragon et al. | 128/419 PG |
| 4,788,980 A | 12/1988 | Mann et al. | 128/419 PG |
| 4,940,052 A | 7/1990 | Mann et al. | 128/419 PG |
| 4,969,467 A | 11/1990 | Callaghan et al. | 128/419 PG |
| 5,350,410 A | 9/1994 | Kleks et al. | 607/28 |
| 5,411,533 A | 5/1995 | Dubreuil et al. | 607/28 |
| 5,466,254 A | 11/1995 | Helland | 607/123 |
| 5,573,550 A | 11/1996 | Zadeh et al. | 607/28 |
| 5,685,315 A | 11/1997 | McClure et al. | 128/708 |
| 5,766,229 A | 6/1998 | Bornzin | 607/28 |
| 5,778,881 A | 7/1998 | Sun et al. | 128/696 |
| 5,785,660 A | 7/1998 | Van Lake et al. | 600/523 |
| 5,810,730 A | 9/1998 | Swartz et al. | 600/434 |
| 5,855,594 A | 1/1999 | Olive et al. | 607/28 |
| 6,038,474 A | 3/2000 | Zhu et al. | 607/9 |

OTHER PUBLICATIONS

Wilber, David.J., et al., Catecholamine Sensitive right Ventricular Outflow Tract Tachycardia: Intraoperative Mapping and Ablation of a Free–Wall Focus, PACE, vol. 12, pp: 1851–1856 (Dec. 1989).

Paul, Vince, et al., Closed Loop Control of Rate Adaptive Pacing: Clinical Assessment of a System Analyzing the Ventricular Depolarization Gradient, PACE, vol. 12, pp: 1896–1902 (Dec. 1989).

Belz, Michael K., et al., The Effect of Left Ventricular Intracavitary Volume on the Unipolar Electrogram, PACE, vol. 16, pp: 1842–1852 (Sep. 1993).

Schuchert, Andreas, et al., Effects of Body Position and Exercise on Evoked Response Signal for Automatic Threshold Activation, PACE, vol. 22, pp: 1476–140 (Oct. 1999).

Economides, Apollo P., et al., The Ventricular Intracardiac Unipolar Paced–Evoked Potential in an Isolated Animal Heart, PACE, vol. 11, pp: 203–213 (Feb. 1988).

Furukawa, Tetshushi, et al., Rapid Assessment of Rate and Antiarrhythmic Drug Effect on the Myocardium Using Asymmetric Biphasic Pulse Stimulation, PACE, vol. 12, Part I, pp: 52–64 (Jan. 1989).

Singer, Igor et al., Effects of Stress and Beta$_1$ Blockade on the Ventricular Depolarization Gradient of the Rate Modulating Pacemaker, vol. 14, pp: 460–469 (Mar. 1991).

Lasaridis, Kyriakos, et al., Influence of Propranolol on the Ventricular Depolarization Gradient, PACE, vol. 14, Part I, pp: 787–792 (May 1991).

Lofland, Gary K., MD, et al., The Local Unipolar Depolarization Complex: A Quantitative Electrophysiologic Index of Irreversible Myocardial Ischemic Injuyry, Surgical Forum, vol. XXXV, 40$^{th}$ Annual Session, pp: 269–271 (Oct. 1984).

Cameron, Douglas, MD, et al., Effect of Body Position on R–Wave and Evoked Response, PACE, vol. 20, ;;: 1109 (Apr. 1997).

*Primary Examiner*—Scott M. Getzow

(57) ABSTRACT

A system and associated method for acquiring, storing, and displaying evoked response signal features for the purposes of monitoring evoked response variability and evaluating the performance of automatic capture. The system further acquires, stores, and displays the number of suspected fusion events for the purpose of improving fusion avoidance through either automatic modification to fusion avoidance mechanisms or by providing a clinician with diagnostic information helpful in selecting programmable operating parameters.

33 Claims, 9 Drawing Sheets

CARDIAC STIMULATION DEVICE AND METHOD FOR STORING DIAGNOSTIC DATA IN AN AUTOMATIC CAPTURE SYSTEM

FIELD OF THE INVENTION

The present invention relates in general to an implantable cardiac stimulation device capable of performing automatic capture. More specifically, the present invention is directed to a cardiac stimulation system and associated method for acquiring, storing, and displaying an evoked response feature log and a fusion event counter.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture." In early pacemakers, a fixed, high-energy pacing pulse was delivered to ensure capture. While this approach is straightforward, it quickly depletes battery energy and can result in patient discomfort due to extraneous stimulation of surrounding skeletal muscle tissue.

The capture "threshold" is defined as the lowest stimulation pulse energy at which capture occurs. By stimulating the heart chambers at or just above threshold, comfortable and effective cardiac stimulation is provided without unnecessary depletion of battery energy. Threshold, however, is extremely variable from patient-to-patient due to variations in electrode systems used, electrode positioning, physiological and anatomical variations of the heart itself, and so on. Furthermore, threshold will vary over time within a patient as, for example, fibrotic encapsulation of the electrode occurs during the first few weeks after surgery. Fluctuations may even occur over the course of a day or with changes in medical therapy or disease state.

Hence, techniques for monitoring the cardiac activity following delivery of a stimulation pulse have been incorporated in modern pacemakers in order to verify that capture has indeed occurred. If a loss of capture is detected by such "capture-verification" algorithms, the output is automatically increased until capture is restored. A threshold test is then performed by the cardiac stimulation device in order to re-determine the threshold and automatically adjust the stimulating pulse output.

This approach, referred to as "automatic capture", improves the cardiac stimulation device performance in at least four ways: 1) by verifying that the stimulation pulse delivered to the patient's heart has been effective, 2) by maintaining the stimulation pulse output at the lowest level possible thus 3) greatly increasing the device's battery longevity by conserving the energy used to generate stimulation pulses yet 4) always protecting the patient by providing a significantly higher output back-up pulse in the setting of loss of capture associated with the primary pulse.

One implemented technique for verifying capture automatically by an implantable stimulation device involves monitoring the internal myocardial electrogram (EGM) signal received on the cardiac stimulation and sensing electrodes. When a stimulation pulse is delivered to the heart, the EGM signals that are manifest concurrent with depolarization of the myocardium are examined. When capture occurs, an "evoked response" may be detected by special evoked response detection circuitry. The evoked response is the intracardiac atrial or ventricular depolarization that is observed as the P-wave or R-wave, respectively, on the surface ECG. Detection of an evoked response indicates electrical activation of the respective cardiac tissue by the stimulating pulse. The depolarization of the heart tissue in response to the heart's natural pacemaking function is referred to as an "intrinsic response".

Through sampling and signal processing algorithms, the presence of an evoked response following a stimulation pulse is determined. A very short blanking period, or period of absolute refractoriness, following the stimulation pulse is applied to the evoked response sensing circuit immediately following the stimulation pulse to minimize or block out the stimulation pulse artifact. This blanking period is followed by a special evoked response detection window, commonly 15 to 60 ms in duration, wherein the evoked response sensing circuit looks for an evoked response. For example, if a stimulation pulse is applied to the ventricle, an R-wave sensed by a special evoked response detection circuit of the pacemaker immediately following application of the ventricular stimulation pulse evidences capture of the ventricles.

If no evoked response is detected, a high-energy back-up stimulation pulse is delivered to the heart very shortly after the primary ineffective stimulus, typically within 60–100 ms of the primary pulse, in order to maintain the desired heart rate. If the loss of capture is sustained for more than one cardiac cycle, an automatic threshold test may be invoked in order to re-determine the minimum pulse energy required to capture the heart. Threshold tests may also be performed on a periodic basis, for example daily or weekly. An exemplary automatic threshold determination procedure is performed by first increasing the stimulation pulse output level to a relatively high predetermined testing level at which capture is certain to occur. Thereafter, the output level is progressively decremented until capture is lost. The stimulation pulse energy is then set to a level safely above the lowest output level at which capture was attained. Thus, reliable capture verification is of utmost importance in proper determination of the threshold.

One signal that interferes with the detection of an evoked response, and potentially the most difficult for which to compensate because it is usually present in varying degrees, is lead polarization. A lead-tissue interface is that point at which an electrode of the pacemaker lead contacts the cardiac tissue. Lead polarization is commonly caused by electrochemical reactions that occur at the lead-tissue interface due to application of an electrical stimulation pulse across the interface. If the evoked response is sensed through the same lead electrodes through which the stimulation pulses are delivered, the resulting polarization signal, also referred to as an "afterpotential", formed at the electrode can corrupt the evoked response signal that is sensed by the sensing circuits. This undesirable situation occurs often because the polarization signal can be three or more orders of magnitude greater than the evoked response. Furthermore, the lead polarization signal is not easily characterized; it is a complex function of the lead materials, lead geometry, tissue impedance, stimulation energy and other variables.

In order to verify that an evoked response is readily recognized during automatic capture verification or threshold testing, calibration methods are employed for measuring a characteristic of the post-stimulation signal, such as peak amplitude, slope, or the signal integral. Capture detection criteria can be determined by measuring the magnitude of a selected signal characteristic, or "signal feature," during an evoked response and during pure polarization associated with non-capture.

Therefore, the post-stimulation signal after delivery of a stimulation pulse known to effectively capture the heart is evaluated to determine an evoked response signal feature. The post-stimulation signal after delivery of a stimulation pulse known not to capture the heart, e.g., by delivering the pulse during myocardial refractory when capture is impossible, is also evaluated. The difference between the evoked response signal features and the polarization signal features, is used to verify the presence of capture.

However, although the variability of the evoked response signal has been acknowledged, there is currently no way of ascertaining that the evoked response signal characteristic, upon which capture detection is based, does not change over time, regardless of stability in threshold.

Although calibration methods may be repeated in order to update the threshold detection criteria, it may not be desirable to do so because the automatic capture algorithm may have to be suspended during calibration. Calibration normally is performed in the clinic while automatic capture is disabled and under the supervision of a clinician. The clinician monitoring the calibration process may verify that the correct signals are sensed during the calibration process and that automatic capture is functioning properly afterward.

Another difficulty encountered in detecting an evoked response during automatic capture verification is the incidence of "fusion." Fusion occurs when a stimulation pulse is delivered nearly simultaneously with a late intrinsic depolarization that goes undetected. Both the stimulation pulse and the intrinsic depolarization may contribute to the overall depolarization. The EMG signal during a fusion event becomes distorted causing the P-wave or R-wave to go undetected by the capture verification routine. A backup stimulation pulse and threshold test may be invoked when not clinically necessary.

Similarly, a "pseudo-fusion" event occurs when a stimulation pulse immediately follows a late intrinsic depolarization. The stimulation pulse does not contribute to the depolarization of the tissue but does obscure the EMG signal causing the R-wave or P-wave to go undetected, again triggering a back-up stimulation pulse and a threshold test.

Methods for determining when fusion or pseudo-fusion is suspected as the cause of a loss of capture detection have been proposed. If fusion is suspected, corrective actions may be taken by adjusting stimulation timing parameters in a way that might avoid fusion in the future, for example by shortening the pacing interval. Knowing the frequency at which fusion events, or suspected fusion events, occur would be useful to a physician in selecting operating parameters related to stimulation timing and automatic capture detection or in improving the methods by which fusion is detected or avoided.

It would therefore be desirable to periodically re-evaluate, in a cardiac stimulation device possessing automatic capture verification methods, the evoked response signal features. A log of the evoked response signal features may then be stored in memory and available for later display or analysis. Examination of the variability of the evoked response signal features over time, as well as the polarization signal features associated with loss of capture, will be useful to a clinician and scientist in evaluating the performance of automatic capture and in fine tuning the automatic capture operating parameters in individual patients. Examination of the variability of the evoked response can also be valuable in monitoring the electrophysiologic status of the patient. It would also be desirable to monitor the frequency of fusion events. If a high frequency of fusion is found, the corrective actions for avoiding fusion could be altered to enhance fusion avoidance.

SUMMARY OF THE INVENTION

The present invention addresses these and other needs by providing a cardiac stimulation device equipped with a "feature log," wherein each time a threshold test is performed, evoked response signal features and loss of capture signal features are evaluated and stored. The evoked response signal features, accumulated over time, can then be displayed and examined to assess evoked response variability for the purposes of evaluating and improving automatic capture performance and for the purpose of monitoring a patient's electrophysiological status. The cardiac stimulation device also provides a "fusion counter" that allows the frequency of fusion to be monitored. Adjustments to fusion avoidance mechanisms may be made in response to a high incidence of fusion.

The foregoing and other features and advantages of the present invention are achieved by providing a cardiac stimulation system that includes an implantable device to sense cardiac signals and deliver stimulation therapy, and an external device to communicate with the implantable device via a telemetry circuit to send and/or receive programmed operating parameters and acquired cardiac data.

The implantable device is equipped with cardiac data acquisition capabilities. A preferred embodiment of the stimulation device includes a control system for controlling the operation of the device and executing various test algorithms such as capture verification, threshold testing, and fusion detection. The stimulation device further includes a set of leads for receiving cardiac signals and for delivering atrial and ventricular stimulation pulses; a set of sensing circuits comprised of sense amplifiers for sensing and amplifying the cardiac signals; and pulse generators for generating atrial and ventricular stimulation pulses. In addition, the stimulation device includes memory for storing operational parameters for the control system, and for storing acquired data in the feature log and fusion counter.

The stimulation device also includes a telemetry circuit for communicating with an external device. The external device preferably can be a user interface, such as a keyboard, mouse, or touch screen; a control system for controlling the operation of functions or tests carried out by the external programmer; a memory for storing control programs, operational parameters, or data received from the implantable device; and/or a display apparatus such an LCD screen or a printer. The external programmer also includes a telemetry unit for transmitting data to and receiving data from the implanted stimulation device.

The cardiac stimulation device of the present invention is capable of performing capture verification and threshold testing with the added ability of determining a number of post-stimulation signal features and storing these features in memory as a vector. To this end, the stimulation device includes an algorithm for acquiring post-stimulation EMG signals occurring within a "detection window" applied during threshold testing. From the acquired signals, the algorithm determines one or more signal features. These features are stored in a multi-byte feature vector along with stimulation parameter information and the date and time at which the feature vector was collected.

In a preferred embodiment, two feature vectors are acquired for the first two evoked response signals occurring during a threshold test, and two more feature vectors are acquired for two loss of capture signals occurring during the threshold test. The feature vectors may be acquired during threshold testing performed in response to loss of capture, or during periodic threshold testing, when automatic capture is enabled. If automatic capture is disabled, the feature vectors may be acquired by performing a threshold test at scheduled intervals.

The stored feature vectors may be downloaded to the external programmer at any time by a clinician. The signal features may be displayed graphically over time so that the clinician can evaluate variability of the evoked response. The signal feature data may also be statistically analyzed to determine variability or other signal behavior. Statistical reports may also be displayed on the external programmer.

The fusion counter included in the present invention is implemented in conjunction with a fusion detection algorithm. The fusion detection algorithm is executed in response to a loss of capture detection when automatic capture is enabled. Each time the fusion detection algorithm determines that fusion is suspected to have caused the loss of capture detection, the fusion counter is incremented. The number of suspected fusion events is then available to the automatic algorithms of the stimulation device for the purpose of adjusting fusion avoidance mechanisms as necessary, or can be downloaded and displayed on an external device to be evaluated by a clinician. The clinician may then adjust programmable operating parameters as appropriate for improving fusion detection and avoidance.

Thus, the present invention provides a system and associated methods for acquiring, storing, and displaying evoked response signal features for the purposes of monitoring evoked response variability and evaluating the performance of automatic capture. The present invention further provides a method for acquiring, storing, and displaying the number of suspected fusion events for the purpose of improving fusion avoidance through either automatic modification to fusion avoidance mechanisms or by providing a clinician with diagnostic information helpful in selecting programmable operating parameters.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at providing an evoked response feature log and a fusion counter. A general cardiac stimulation device will thus be described in conjunction with FIGS. 1 and 2, in which the concepts included in the present invention could be implemented. It is recognized, however, that numerous variations of such a device exist in which the methods of the present invention could be implemented without deviating from the scope of the present invention.

Figure 1:
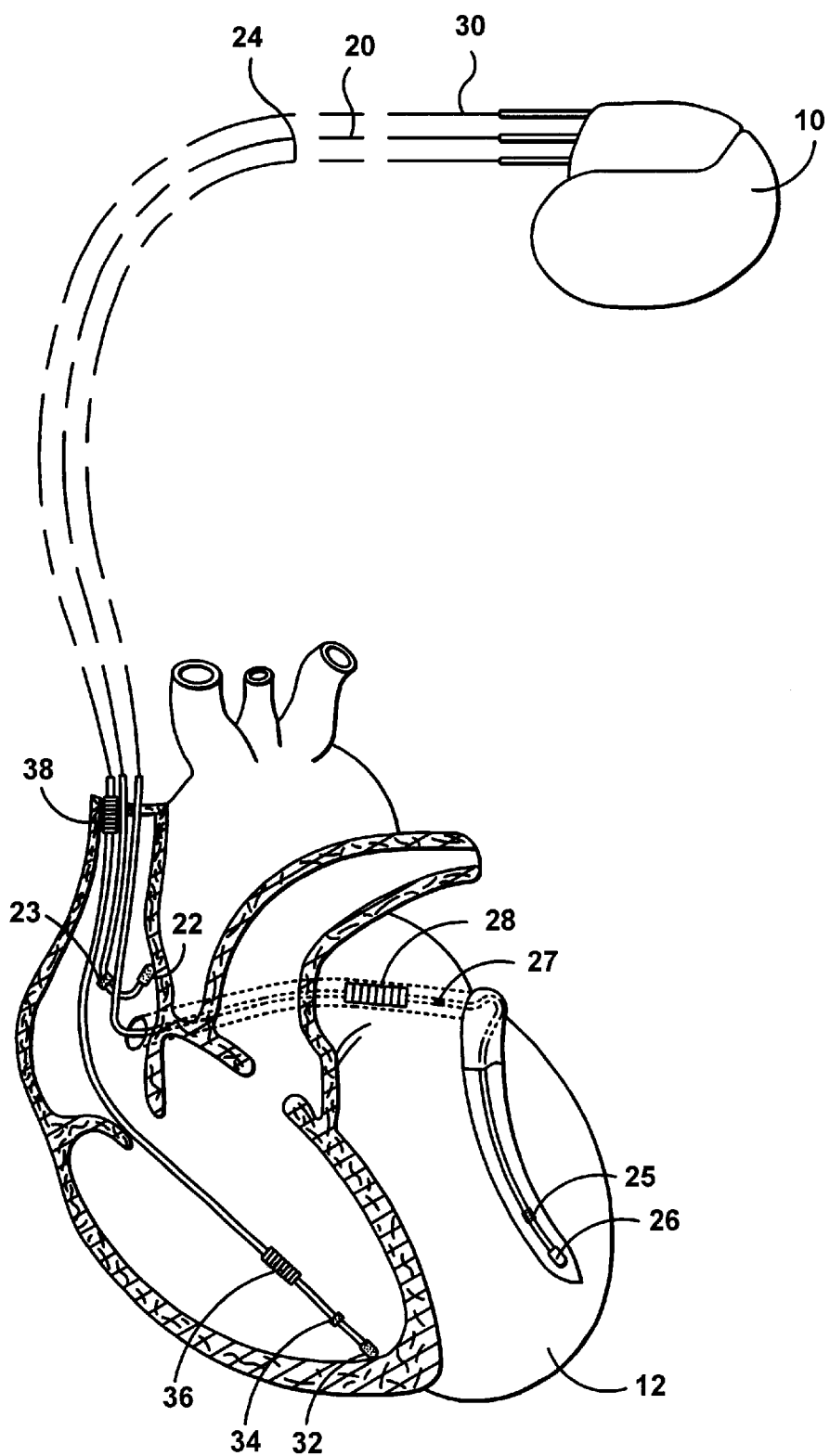
FIG. 1 is a simplified diagram illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. For a more detailed description of a coronary sinus lead, reference is made to U.S. Pat. No. 5,466,254, titled "Coronary Sinus Lead with Atrial Sensing Capability" (Helland), which is incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
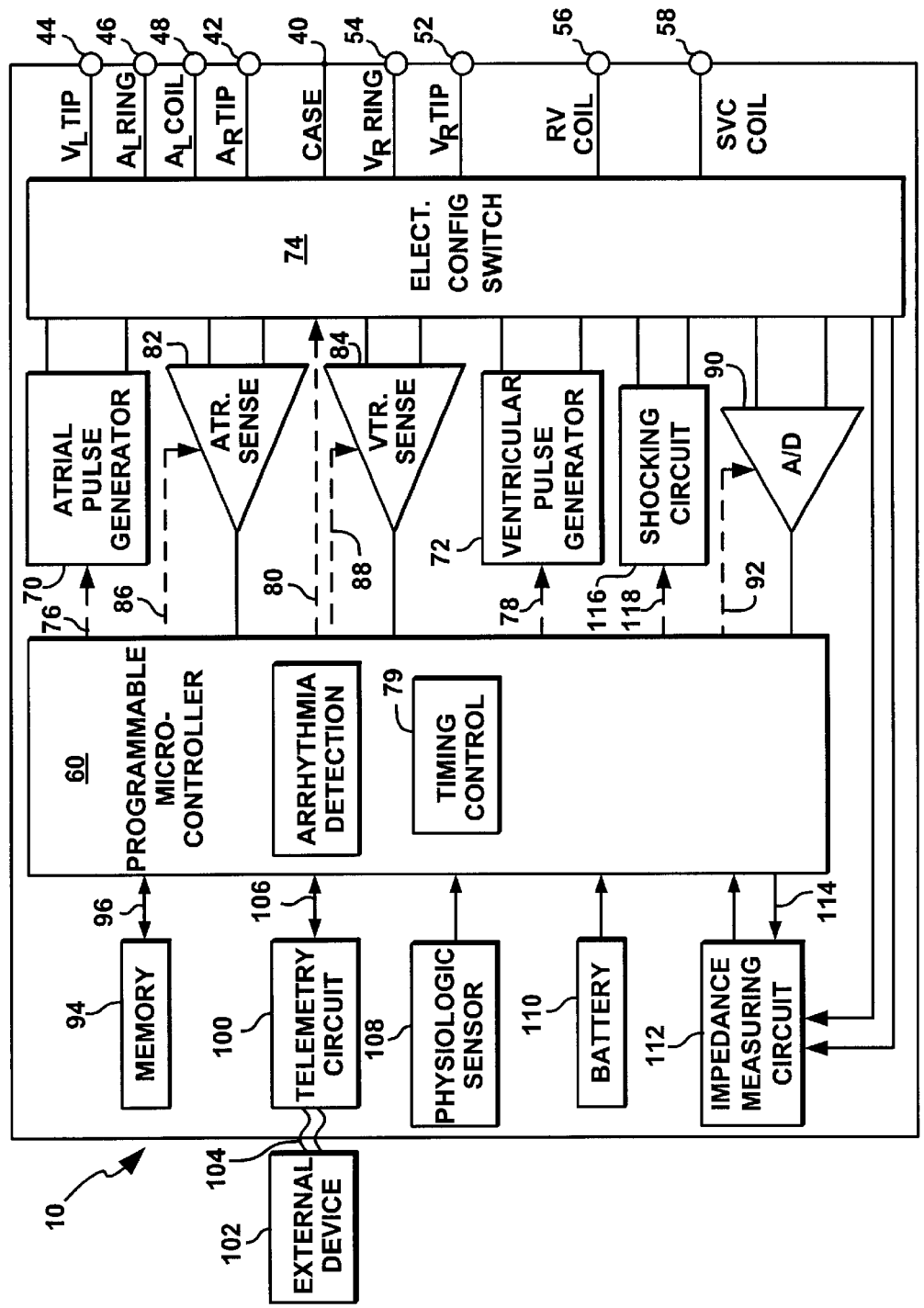
FIG. 2 is a functional block diagram of a multi-chamber implantable stimulation device illustrating the basic elements of a stimulation device that can provide cardioversion, defibrillation and pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector having a plurality of terminals 42, 43, 44, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the atrial ring electrode 23.

To achieve left chamber sensing, pacing, and shocking, the connector includes at least a left ventricular tip terminal ($V_L$ TIP) 44, a left atrial ring terminal ($A_L$ RING) 46, and a left atrial shocking coil terminal ($A_L$ COIL) 48, which are adapted for connection to the left ventricular tip electrode 26, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the present invention include the microprocessor-based control system of U.S. Pat. No. 4,940,052 (Mann et. al), which is incorporated herein by reference. For a more detailed description of the various timing intervals used within the stimulation device and their inter-relationship, reference is made to U.S. Pat. 4,788,980 (Mann et. al), which is incorporated herein by reference.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches (not shown) as is known in the art. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Stimulation during pacing can be performed in a bipolar mode in devices combining pacing and cardioversion/defibrillation functions because unipolar stimulation may interfere with arrhythmia detection. Hence, in one embodiment of the present invention, the switch bank 74 is configured such that: right atrial pacing and sensing is performed in a bipolar fashion between the right atrial tip electrode 22 and right atrial ring electrode 23; right ventricular pacing and sensing is performed in a bipolar fashion between right ventricular tip electrode 32 and right ventricular ring electrode 34; and left ventricular pacing and sensing is performed in a bipolar fashion between coronary sinus tip electrode 26 and the coronary sinus ring electrode 27. Right ventricular sensing may alternatively be configured between the right ventricular coil electrode 36 and the right ventricular ring electrode 34. Bipolar sensing may also be achieved using an integrated bipolar lead wherein the right ventricular coil electrode 36 and right ventricular ring electrode 34 are electrically coupled within the right ventricular lead body 30. Bipolar sensing is then performed between the right ventricular tip electrode 32 and the coupled right ventricular coil electrode 36 and right ventricular ring electrode 34. The electrode combinations used for pacing and sensing are not critical to the present invention. Rather, any electrode combination that allows acceptable stimulation and sensing thresholds may be used. By employing the right ventricular coil electrode 36, possibly in combination with right ventricular ring electrode 34, the electrode surface during sensing is increased, advantageously reducing the effects of lead polarization. Other techniques of reducing lead polarization such as titanium nitride coating may also be used to improve the operation of the present invention.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation. For a more detailed description of a sensing circuit, reference is made to U.S. Pat. No. 5,573,550, titled "Implantable Stimulation Device having a Low Noise, Low Power, Precision Amplifier for Amplifying Cardiac Signals" (Zadeh et al.), which is incorporated herein by reference. For a more detailed description of an automatic sensitivity control system, reference is made to U.S. Pat. No. 5,685,315, titled "Cardiac Arrhythmia Detection System for an Implantable Stimulation Device" (McClure et. al), which is incorporated herein by reference.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.), in order to determine the type of remedial therapy that is needed (e.g. bradycardia pacing , antitachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". When automatic capture is enabled, the microcontroller 60 searches for a depolarization signal following a stimulation pulse during a "detection window" set by timing control circuitry 79 within microcontroller 60. The microcontroller 60 enables the data acquisition system 90 via control signal 92 to sample the cardiac signal that falls in the capture detection window. The sampled signal is evaluated to determine if it is an evoked response signal based on its amplitude, peak slope, or another signal feature or combination of features. The detection of an evoked response during the detection window indicates that capture has occurred.

Capture detection may occur on a beat-by-beat basis or on a sampled basis. When loss of capture is detected, a safety, back-up pulse is delivered shortly after the ineffective primary pulse in order to maintain a desired heart rate. Preferably, a capture threshold search is then performed in order to re-determine the threshold and appropriately adjust the stimulation pulse energy. A capture threshold search is also performed on a periodic basis, preferably once a day during at least the acute phase (e.g., the first 30 days) and less frequently thereafter. A capture threshold search would begin at a desired starting point (either a high energy level or the level at which capture is currently occurring) and decrease the energy level until capture is lost. The output level is then increased again until capture is regained. The lowest output level at which sustained capture is regained is known as the capture threshold. Thereafter, the stimulation output is adjusted to a level equal to the capture threshold plus a working margin. The implementation of capture detection circuitry and algorithms are well known. See for example, U.S. Pat. No. 5,350,410 (Mann et al.), which is incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

Preferably, designated blocks of memory cells located in memory 94 may be used to store cardiac data. In accordance with the present invention, a block of memory cells is designated to store evoked response and loss of capture signal feature vectors in a feature log. Another block of memory cells is designated to store the number of suspected fusion events in a fusion counter. The contents of the feature log and the fusion counter may be advantageously transmitted to the external device 102 for display in graphical or report format.

The stimulation device 10 preferably includes a physiologic sensor 108, commonly referred to as a "rate-responsive" sensor because it is typically used to adjust stimulation rate according to the exercise state of the patient. In a preferred embodiment of the present invention, the physiologic sensor 108 is an activity sensor, which provides an output, received by microcontroller 60, related to the activity level of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V-V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected. Accordingly, the stimulation device 10 can employ lithium/silver vanadium oxide batteries.

As further illustrated in FIG. 2, the stimulation device 10 is shown to include an impedance measuring circuit 112 which is enabled by the microcontroller 60 by means of a control signal 114.

If it is a primary function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 540 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
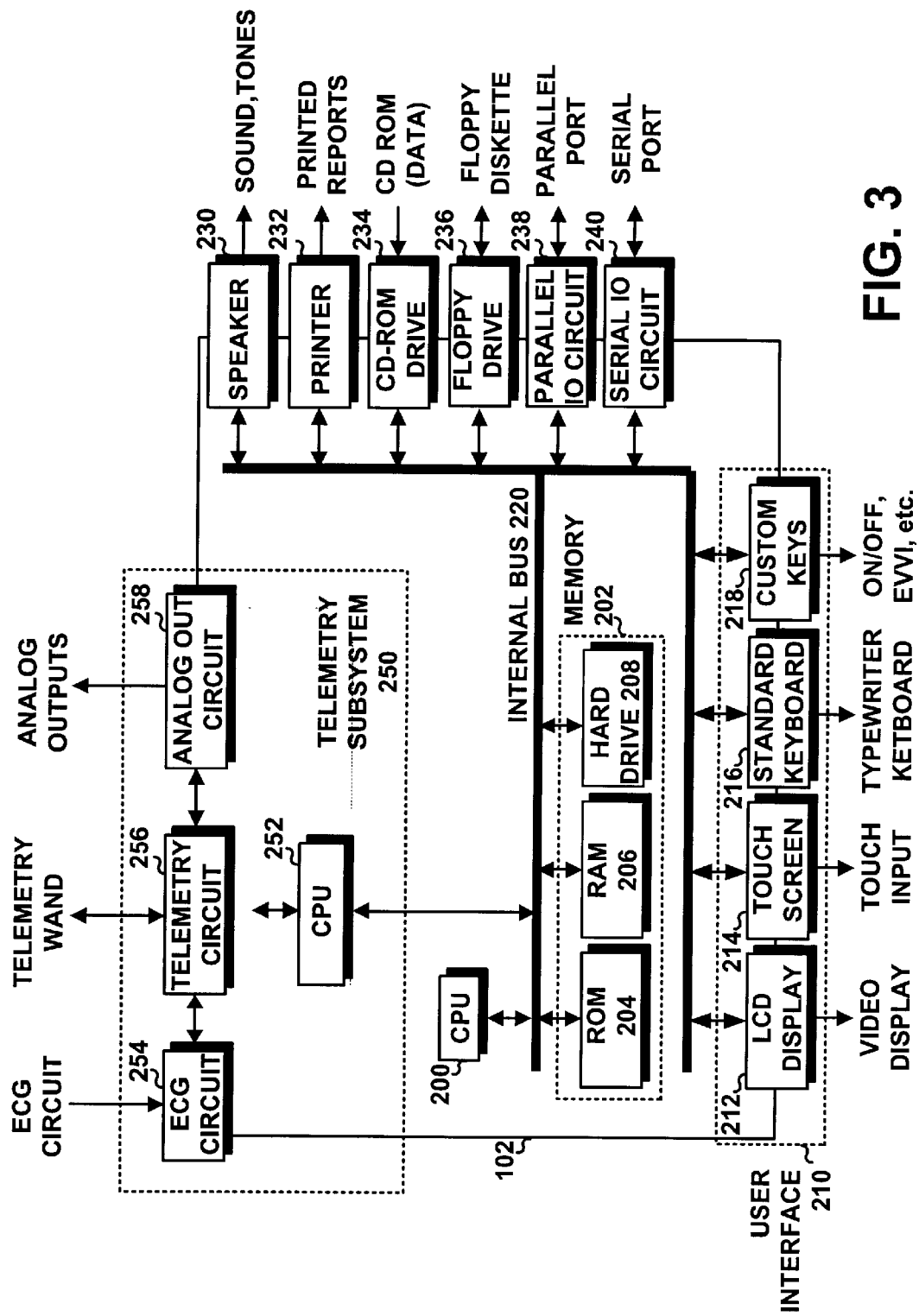
FIG. 3 is a functional block diagram illustrating basic elements of an external device that can send and receive commands or data through telemetric communication with the implantable stimulation device of FIG. 2.

FIG. 3 illustrates a simplified block diagram of an exemplary external programming device 102 that communicates with the stimulation device 10 through a telemetry circuit 100. The external device 102 comprises a central processing unit (CPU) 200 that controls the operations carried out by the external device 102, such as programming the operating parameters of the device 10 or carrying out various testing or diagnostic functions. Testing and diagnostic functions preferably include evoked response sensitivity testing.

CPU 200 is in communication with a memory 202 via internal bus 220. The memory 202 may include a read-only memory (ROM) 204, a random access memory (RAM) 206, or a hard drive 208. Operating parameters and algorithms controlling the programming and testing functions carried out by the external device 102 may be stored in memory 202 and accessed by CPU 200.

The external device 102 is also equipped with a user interface 210 that allows connection to an LCD display 212, a touch screen 214, a key board 216, and/or custom keys 218 that control a specific function or deliver a specific command automatically. Each component of the user interface 212 is also in communication with the CPU 200 and memory 202 via the internal bus 220 to allow user input, such as programming commands delivered using the touch screen 214, keyboard 216, or custom keys 218, to be received by the CPU 200 and/or stored in memory 202.

The programming selections made by a user and results of programming or testing operations may be displayed on the video display 212. Messages relating to the success of the programming command, recommended programmed settings, or warnings to the user regarding selected parameters may also be displayed on the video display 212.

The CPU 200 and memory 202 are also in communication with various input/output interfaces via the internal bus 220 that may include: a speaker 230 for delivering sounds or tones during the programming procedures; a printer 232 for printing results of programming or testing operations; a CD-ROM drive 234 and floppy drive 236 to which data from testing or programming operations may be written; and a parallel input/output port 238 and a serial input/output port 240 to allow connection to auxiliary equipment.

The external device 102 is further equipped with a telemetry subsystem 250. The telemetry subsystem 250 includes a central processing unit (CPU) 252 for controlling the transfer of data between the external device 102 and the implanted device 10. Thus, the telemetry CPU 252 is in communication with the internal bus 220 so that data may be transferred between the telemetry subsystem 250, the CPU 200, memory 202, user interface 210, and other input/output interfaces, 230, 232, 234, 236, 238, and 240. The telemetry CPU 252 is connected to at least three interfaces that facilitate the receipt or transmission of data.

Figure 4:
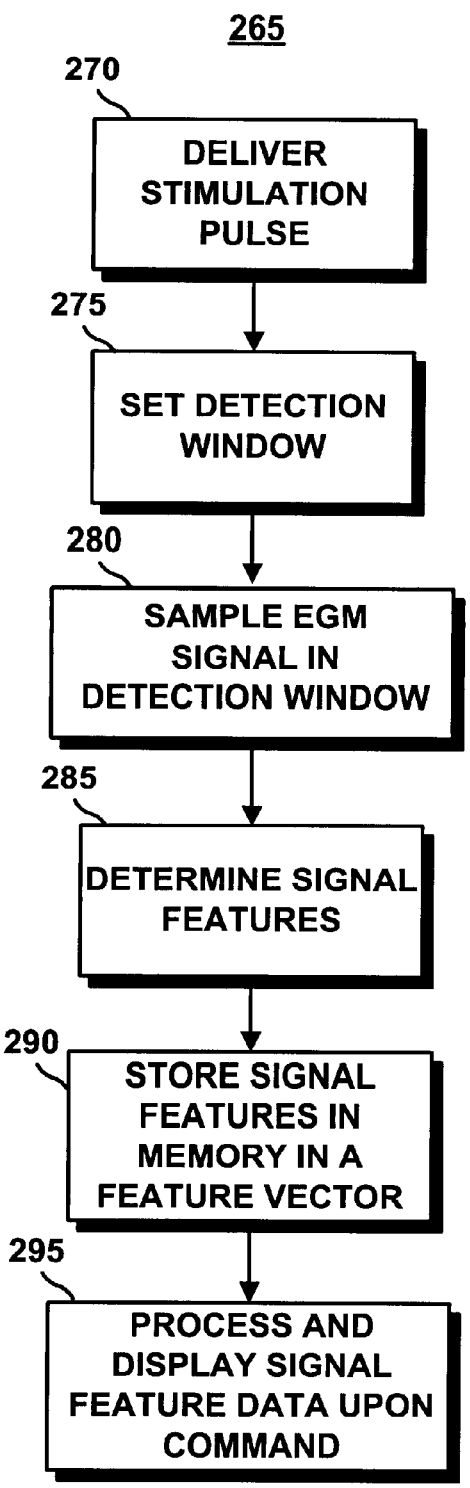
FIG. 4 is a flow chart describing a high level architecture of the operation of one embodiment of the stimulation device of FIGS. 1 and 2, for acquiring, storing, and displaying signal feature data in a feature log.

An ECG circuit interface 254 allows connection to surface ECG leads for collecting a patient's ECG. The ECG may be displayed in real time on the video display 212. A telemetry circuit interface 256 allows connection to a telemetry wand that is placed over the implanted device 10 for receiving or sending data such as cardiac signal data stored in the memory 94 of device 10 or programmed operating parameters received at the user interface 210. An analog output circuit interface 258 allows connection to an analog output port FIG. 4 illustrates a process flow chart that depicts an overview of the operation and features implemented in one embodiment of the stimulation device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The flow chart shown in FIG. 4 illustrates a process 265 that provides an overview of the steps involved in acquiring, storing, and displaying data related to features of an evoked response signal, or a loss of capture signal, following a stimulation pulse. The process 265 illustrates the functions included in a "feature log" as provided by the present invention.

At step 270 of FIG. 4 the implantable device 10 delivers a stimulation pulse to a heart chamber, either in the atria or the ventricles. At step 275, a detection window is set following the stimulation pulse. At step 280, the internal electrogram signal (EGM), received by device 10 using a desired sensing electrode configuration, is sampled during the detection window. A desired set of signal features is determined from the sampled signal at step 285.

At step 290, the signal features are stored in a feature vector along with contextual information regarding the stimulation conditions. At step 295, the signal feature data may be downloaded and displayed on an external device 102 upon receiving a user command. The signal feature data may also be analyzed statistically at step 295 so that statistical reports regarding the variability of any or all signal features may also be displayed.

Figure 5:
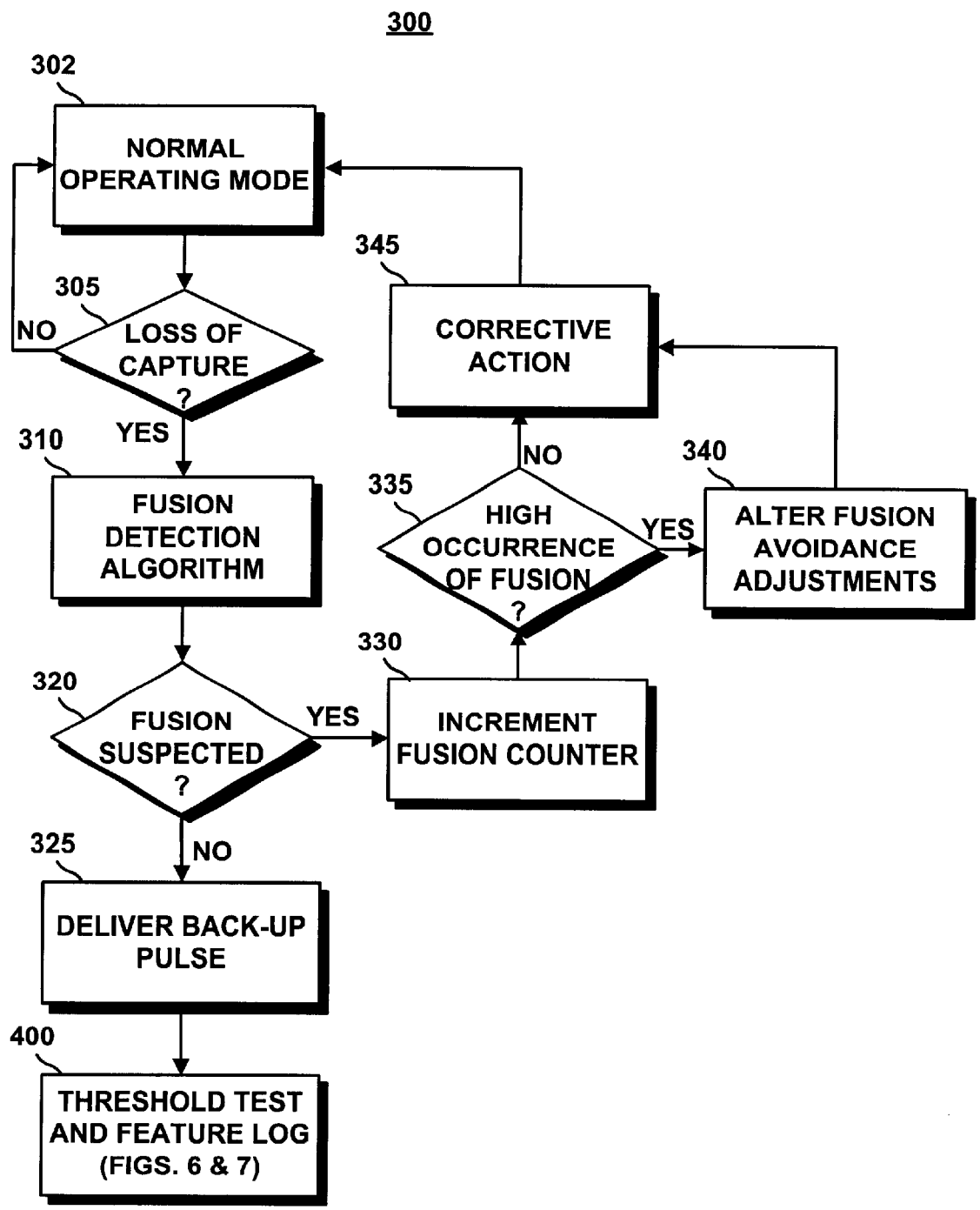
FIG. 5 is a flow chart depicting an overview of the operation of the stimulation device FIGS. 1 and 2 for initiating a feature log algorithm when automatic capture is enabled and for utilizing a fusion event counter.

Evoked response or loss of capture signals sampled and stored in the feature log as shown in FIG. 4 are preferably acquired during a threshold test. The threshold test may be a scheduled test or a test invoked as the result of a detected loss of capture. The process 265 of FIG. 5 provides an overview of how the feature log of FIG. 4 may operate when automatic capture is enabled in device 10. Additional details regarding the steps shown in FIG. 4 will be discussed later in more detail.

FIG. 5 illustrates a process 300 that exemplifies the operation of the stimulation device 10 for initiating a feature log algorithm when automatic capture is enabled and for utilizing a fusion event counter. At step 302 of FIG. 5, the implantable stimulation device 10 operates according to the normally programmed operating parameters for sensing cardiac events and delivering stimulation therapy.

Whenever a stimulation pulse is delivered during this normal operating mode, capture is verified at step 305 using methods known in the art. If loss of capture is detected, a fusion detection algorithm is executed at step 310 to determine if a fusion event is suspected to have caused an inaccurate loss of capture detection. Any adequate method may be used for determining if loss of capture detection is likely to have been caused by a fusion event. The exact method for fusion detection is not critical to the present invention. For details regarding a fusion detection method, reference is made to U.S. Pat. No. 4,969,467 to Callaghan.

If fusion is suspected at decision step 320, a fusion counter, located in memory 94 (FIG. 2), is incremented at step 330. A high occurrence of fusion events is easily recognized by the number of fusion events stored in the fusion counter. The fusion counter can be reset, for example, every ninety days. If a high occurrence of fusion events has been detected, as determined at decision step 335, adjustments are made to avoid fusion at step 340. Otherwise, corrective action to minimize the likelihood of fusion is taken at step 345. The device 10 then returns to the normal operating mode at step 302.

The corrective action taken at step 345 to minimize the likelihood of fusion events is preferably an adjustment to the stimulation parameters that reduces the chances of a stimulation pulse being delivered coincidentally with an intrinsic depolarization. For example, the programmed AV and PV delays may be shortened by a predefined interval such that the ventricular stimulation pulse is delivered earlier in the cardiac cycle and more likely to precede an intrinsic ventricular depolarization. If the fusion counter exceeds a given number of fusion events, such that a high occurrence of fusion is detected at decision step 335, the corrective action made to avoid fusion may be altered at step 340. For example, the AV and PV delays may be shortened even further, the stimulation rate may be increased, or another stimulation parameter or combination of parameters may be adjusted in a way that would enhance fusion avoidance in the future. For details regarding one method for minimizing the interference of fusion with capture verification, reference is made to U.S. Pat. No. 5,766,229 to Bornzin, which is incorporated herein by reference.

If at step 310 the fusion detection algorithm which is executed in response to a loss of capture does not determine that fusion is suspected at decision step 320, the loss of capture detection is presumed to be appropriate. A high-energy, back-up, safety pulse is delivered at step 325. Typically, this safety pulse is delivered at approximately 4.5 V pulse amplitude within 60 to 100 ms following the primary stimulation pulse. A threshold test and evoked response feature log are then executed at step 400. A threshold test may optionally not be performed after every loss of capture detection (step 400). Typically, a sustained loss of capture, defined as loss of capture on two or more consecutive primary pulses, is required before a threshold test is performed.

Figure 6:
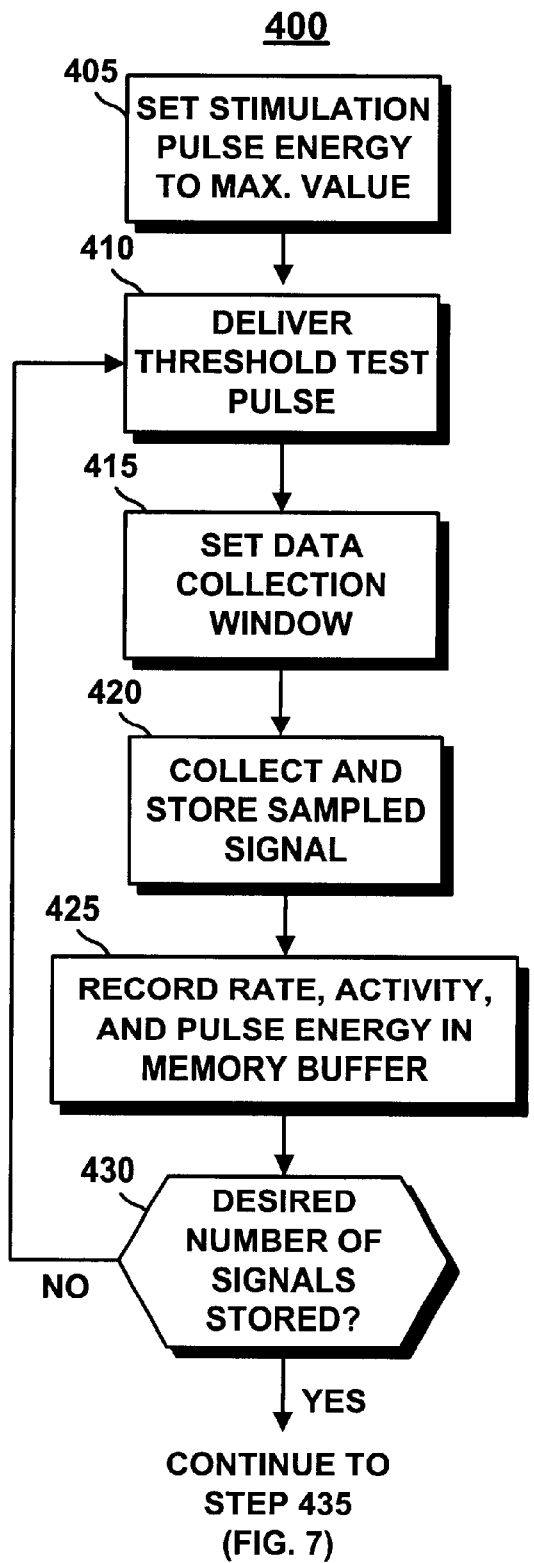
FIGS. 6 and 7 show a flow chart depicting an overview of the operation of the stimulation device FIGS. 1 and 2 for performing a threshold test and feature log.
Figure 7:
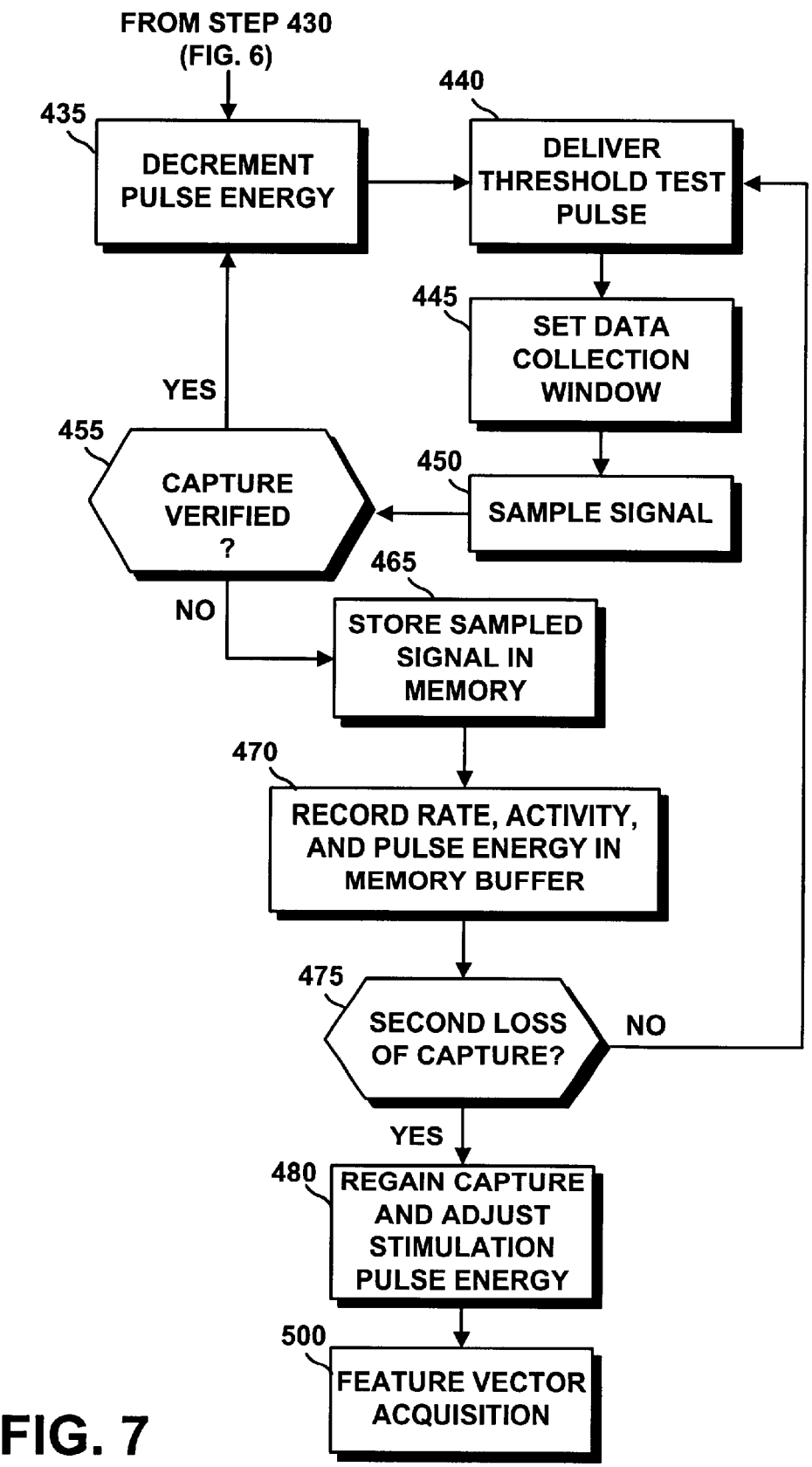

The flow chart shown in FIGS. 6 and 7 illustrates a process implemented by one embodiment of the stimulation device 10 for performing a threshold test and logging an evoked response feature vector as executed at step 400 of FIG. 5. The process, which is also referenced by the numeral 400 for purpose of consistency, will determine the capture threshold and simultaneously sample and store the post-stimulation signal following the first two threshold test pulses resulting in capture and the last two threshold test pulses that fail to capture.

Beginning at step 405, the stimulation pulse energy is set to a level known to ensure capture. Typically, the pulse amplitude is set to approximately 4.5 Volts. At step 410, the first threshold test pulse is delivered. A data collection window is set at step 415 during which the post-stimulation signal is sampled and stored at step 420. The data collection window starts after a short, predefined delay following the threshold test pulse. The duration of the data collection window should be long enough to allow sampling of the evoked response signal and will typically be in the range of 20 to 60 ms in duration.

At step 425, the current stimulation rate, activity level, and pulse energy are stored in a memory buffer. At decision step 430, the microprocessor 60 determines if the desired number of evoked response signals have been sampled and stored. Preferably, two evoked response signals are stored. If the desired number of stored signals has not been reached, the process 400 returns to step 410 to deliver another stimulation pulse, and repeats steps 415 through 430. Once the desired number of evoked response signals has been reached, the process 400 proceeds to step 435, in FIG. 7.

At step 435, the pulse energy is decreased. The pulse energy may be decreased by decrementing either the pulse amplitude or the pulse width. The threshold test pulse is delivered at the decreased pulse energy at step 440, and the data collection window is set at step 445. The post-stimulation signal is sampled at step 450. If capture is verified, as determined at decision step 455, the sampled signal is not stored in memory 94. Rather, the pulse energy is decreased again at step 435, and steps 440 through 455 are repeated until a loss of capture is detected.

When loss of capture is detected at decision step 455, the sampled signal is stored in memory 94 at step 465. At step 470, the stimulation rate, activity level and pulse energy are stored in a corresponding memory buffer. If this is the first loss of capture detection, the process 400 returns to step 440 to repeat step 440 through 470, until two or more loss of capture detections have occurred and the corresponding loss of capture signals have been sampled and stored.

At step 480, the pulse energy is incremented just until sustained capture is regained, and the programmed stimulation pulse energy is adjusted according to the newly determined capture threshold. At step 500, the post-stimulation signal features are determined from the stored signals and written to memory 94 in a signal feature vector.

Figure 8:
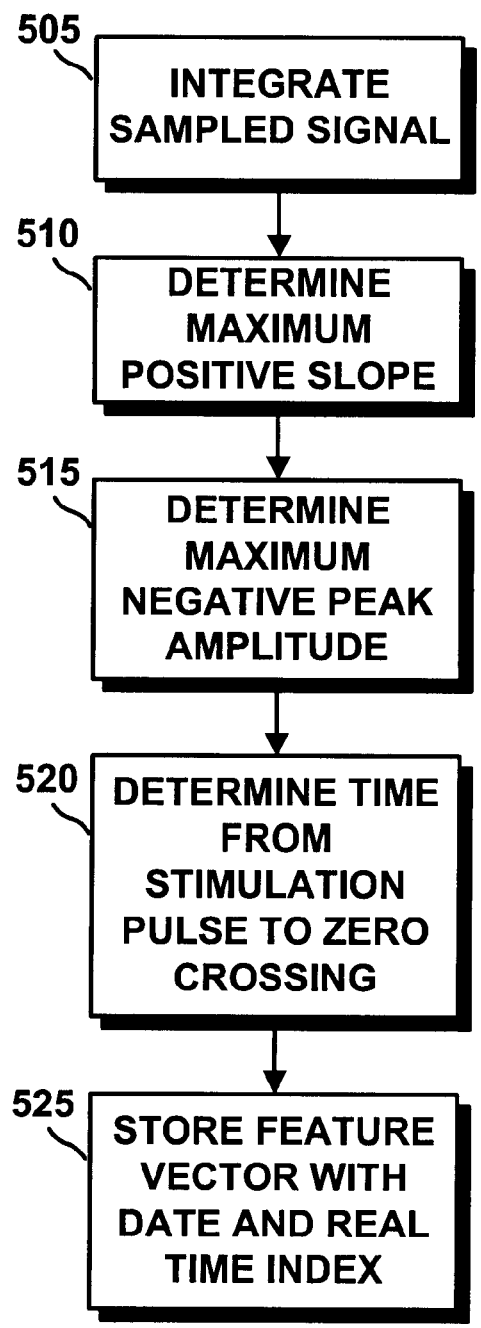
FIG. 8 is a flow chart describing a process implemented by the stimulation device FIGS. 1 and 2 for determining signal features to be stored as a vector in the feature log.

The details of the signal feature vector acquisition process 500 are provided in the flow chart shown in FIG. 8. At step 505, the negative signal samples are integrated to determine the signal integral. At step 510, the maximum positive slope is determined. At step 515, the maximum negative peak amplitude is determined. At step 520, the time from the stimulation pulse to the zero crossing is determined. At step 525, these signals are stored in a feature vector, along with the rate, activity and pulse energy information.

Figure 9:
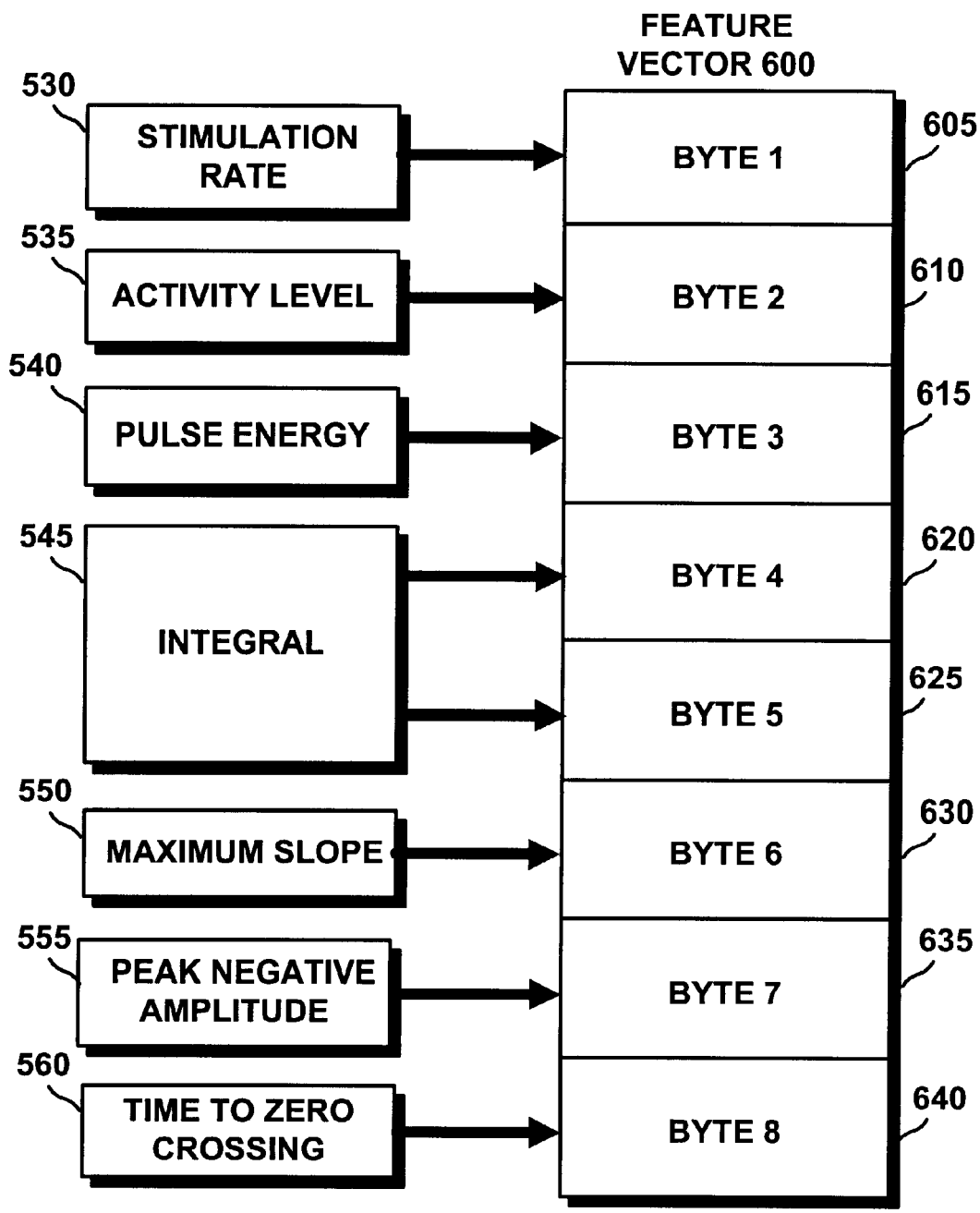
FIG. 9 illustrates a memory format of a feature vector stored in the feature log, pursuant to the process of FIG. 8.

A preferred storage format of the signal feature vector is illustrated in FIG. 9. An 8-byte feature vector 600 is stored for each of the four sampled signals obtained during the threshold test of FIGS. 6 and 7. The signal features and other operating parameter information may be stored as follows: the atrial or ventricular stimulation rate 530 is stored in byte 1 at step 605; the activity level 535 is stored in byte 2 at step 610; the pulse energy 540 (which may be represented by the pulse amplitude setting or the pulse width setting) is stored in byte 3 at step 615; the signal integral 545 is stored in byte 4 at step 620 and byte 5 at step 625; the maximum positive slope 550 is stored in byte 6 at step 630; the peak negative amplitude 555 is stored in byte 7 at step 635; and the time from the stimulation pulse to the zero crossing 560 is stored in byte 8 at step 640. A corresponding date and time index is stored with each feature vector 600.

Preferably, automatic capture and the feature log may be separately enabled or disabled. If automatic capture is disabled, the feature log may be still be enabled to store evoked response signal features during periodic threshold tests. Scheduled threshold testing for the purposes of feature vector acquisition is preferably programmable and may be performed, for example, every eight hours, daily, weekly, etc. The threshold test and feature vector acquisition are performed in the same was as described above in conjunction with FIGS. 6 through 9.

The contents of the feature log and the fusion counter may be downloaded from device 10 to the external device 102 at any time for examination by a clinician. Using the user interface 210, the clinician may deliver a command to the implantable device 10 to retrieve the feature log or fusion counter data. The data is transmitted from implantable device 10 via the telemetry circuit 100 to the external device 102 via the telemetry subsystem 250. The data is preferably displayed on LCD display 212. The feature log data may be displayed graphically as a function of time. The feature log data may be further analyzed statistically for variations using statistical analysis programs stored in memory 202 of external device 102 or memory 94 of implantable device 10. One or more of the signal features stored in the feature vector may be analyzed for variability over time. A full report of all data analysis and desired graphs may be displayed on LCD display 212, and if desired, printed on printer 232.

Thus, a cardiac stimulation system and associated method has been described for acquiring, storing and displaying evoked response signal features, loss of capture signal features, and the number of fusion events. Storing and displaying evoked response signal features allows a clinician to monitor evoked response variability which can be associated with the electrophysiological status of the patient. Storing and displaying evoked response and loss of capture signal data allows a clinician or scientist to evaluate the performance of automatic capture verification and make appropriate adjustments to programmable settings controlling automatic capture or develop improvements in automatic capture techniques. Storing and displaying the number of suspected fusion events allows a clinician to adjust fusion avoidance mechanisms to minimize the likelihood of fusion interfering with automatic capture.

While detailed descriptions of specific embodiments of the present invention have been provided, it would be apparent to those reasonably skilled in the art that numerous variations of acquiring, storing, and displaying signal feature data and the number of fusion events are possible in which the concepts and methods of the present invention may readily be applied. The descriptions provided herein, therefore, are for the sake of illustration and are no way intended to be limiting.

What is claimed is:

1. A method of acquiring and storing cardiac data for use in a stimulation device, the method comprising:
   setting a signal detection window following a stimulation pulse delivered to a cardiac chamber during a threshold test;
   sampling a cardiac signal during the detection window;
   determining a set of signal features from a sampled signal;
   correlating the set of signal features to an evoked response;
   storing the set of signal features;
   generating a statistical analysis based on a stored set of signal features, that is reflective of a variability of the evoked response features over time; and
   displaying the statistical analysis to allow for monitoring the evoked response variability to evaluate automatic capture performance.

2. The method of claim 1, wherein storing the set of signal features comprises storing the set of signal features in a memory vector.

3. The method of claim 2, further comprising performing the threshold test in response to a loss of capture during automatic capture verification.

4. The method of claim 2, further comprising performing the threshold test on a scheduled basis.

5. The method of claim 2, wherein sampling the cardiac signal comprises sampling an evoked response signal.

6. The method of claim 3, wherein sampling the cardiac signal comprises sampling a loss of capture signal.

7. The method of claim 6, wherein determining the set of signal features comprises determining any one or more of the following signal features:
   an integral of negative signal samples;
   a maximum positive slope of the cardiac signal;
   a peak negative amplitude of the cardiac signal; and
   a time from the delivery of the stimulation pulse to a zero crossing of the cardiac signal.

8. The method of claim 5, further comprising sampling the cardiac signal during the detection window, following the delivery of two capturing stimulation pulses.

9. The method of claim 8, further comprising sampling the cardiac signal during the detection window, following the delivery of two stimulation pulses that result in loss of capture so as to correlate the set of signal features to a loss of capture signal.

10. The method of claim 2, wherein storing in the memory vector comprises storing the set of signal features in an 8-byte vector for storing at least one of the following data values:
    a stimulation rate at the time the cardiac signal was sampled;
    an activity level according to a sensed activity at the time the cardiac signal was sampled;
    a stimulation pulse energy associated with the sampled cardiac signal;
    a first part of the integral of negative signal samples;
    a second part of the integral of negative signal samples;
    a maximum positive slope of the cardiac signal;
    a peak negative amplitude of the cardiac signal;
    a time from the delivery of the stimulation pulse to a zero crossing of the cardiac signal.

11. The method of claim 1 wherein generating the statistical analysis comprises determining a variation of one or more cardiac signal features with time.

12. The method of claim 1, further comprising acquiring and storing a number of suspected fusion events.

13. The method of claim 12, wherein acquiring the number of suspected fusion events comprises:
    detecting a plurality of suspected fusion events;
    incrementing a fusion event counter with each suspected fusion event;
    notifying a control system of a high occurrence of fusion events within a given period of time;
    in response to the notifying step, adjusting one or more stimulation parameters, when a predefined number of high fusion events occurrence is detected, to improve fusion avoidance; and
    further comprising resetting the fusion counter after a predefined period of time.

14. The method of claim 13, wherein adjusting one or more stimulation parameters comprises shortening a stimulation rate.

15. The method of claim 13, wherein adjusting one or more stimulation parameters comprises shortening an atrial-ventricular delay.

16. The method of claim 13, wherein adjusting one or more stimulation parameters comprises adjusting one or more automatic capture operating parameters.

17. The method of claim 16 wherein adjusting one or more stimulation parameters comprises adjusting one or more stimulation parameters and one or more automatic capture operating parameters.

18. The method of claim 13, further comprising graphically displaying the number of suspected fusion events.

19. A stimulation device for acquiring and storing cardiac data, comprising:
    a generator that selectively generates stimulation pulses;
    a timing circuit connected to the generator for setting a signal detection window following a delivery of a stimulation pulse to a cardiac chamber during a threshold test;
    a sampler that samples a cardiac signal during the detection window, in response to the delivery of the stimulation pulse;
    a controller, coupled to the sampler, that determines a set of signal features from a sampled signal;
    memory that stores the set of signal features;
    an analyzer, connected to the controller, that generates a statistical analysis based on a stored set of signal features, that is reflective of a variability of the evoked response features over time; and
    a display that displays the statistical analysis, to allow for monitoring the evoked response variability to evaluate automatic capture performance.

20. The stimulation device of claim 19, wherein the memory stores the set of signal features in a memory vector.

21. The stimulation device of claim 20, wherein the controller performs the threshold test in response to a loss of capture during automatic capture verification.

22. The stimulation device of claim 21, wherein the sampled cardiac signal comprises a loss of capture signal.

23. The stimulation device of claim 22, wherein the set of signal features comprises any one or more of the following signal features:
    an integral of negative signal samples;
    a maximum positive slope of the cardiac signal;
    a peak negative amplitude of the cardiac signal;
    a time from the delivery of the stimulation pulse to a zero crossing of the cardiac signal.

24. The stimulation device of claim 20, wherein the controller performs the threshold test on a scheduled basis.

25. The stimulation device of claim 20, wherein the sampled cardiac signal comprises an evoked response signal.

26. The stimulation device of claim 25, wherein the sampler samples the cardiac signal during the detection window, following the delivery of two capturing stimulation pulses, so as to correlate the set of signal features to the evoked response; and wherein the sampler further samples the cardiac signal during the detection window, following the delivery of two stimulation pulses that result in loss of capture so as to correlate the set of signal features to a loss of capture signal.

27. The stimulation device of claim 20, wherein the memory vector comprises an 8-byte vector that stores at least one of the following data values:

a stimulation rate at the time the cardiac signal was sampled;

an activity level according to a sensed activity at the time the cardiac signal was sampled;

a stimulation pulse energy associated with the sampled cardiac signal;

a first part of the integral of negative signal samples;

a second part of the integral of negative signal samples;

a maximum positive slope of the cardiac signal;

a peak negative amplitude of the cardiac signal;

a time from the delivery of the stimulation pulse to a zero crossing of the cardiac signal.

28. The stimulation device of claim 27, further comprising:

means for detecting a plurality of suspected fusion events;

means for incrementing a fusion event counter with each suspected fusion event;

means for notifying a control system of a high occurrence of fusion events within a given period of time; and means for improving fusion avoidance by adjusting one or more stimulation parameters when a predefined number of high fusion events occurrence is reached.

29. The stimulation device of claim 28, wherein the fusion avoidance improving means shortens a stimulation rate.

30. The stimulation device of claim 28, wherein the fusion avoidance improving means shortens an atrial. ventricular delay.

31. The method of claim 28, wherein the fusion avoidance improving means adjusts one or more automatic capture operating parameters.

32. A stimulation device for acquiring and displaying cardiac data, comprising:

means for delivering a stimulation pulse to a cardiac chamber during a threshold test;

means for setting a signal detection window following the delivery of the stimulation pulse;

means for sampling a cardiac signal during the detection window;

means for defining a set of signal features from a sampled signal;

means for generating a statistical analysis based on a set of signal features, that is reflective of a variability of the evoked response features over time; and means for displaying the statistical analysis to allow for monitoring the evoked response variability to evaluate automatic capture performance.

33. The stimulation device of claim 32, further comprising means for performing the threshold test in response to a loss of capture during automatic capture verification.

* * * * *